United States Patent [19]

Ostergard et al.

[11] Patent Number: 5,715,608
[45] Date of Patent: Feb. 10, 1998

[54] GYNECOLOGICAL GONIOMETER

[76] Inventors: Donald R. Ostergard, 38 Rocking Horse Rd., Rancho Palos Verdes, Calif. 90274; Albert E. Brooks, 5358 Annapolis Ct., Ventura, Calif. 93003

[21] Appl. No.: 573,688

[22] Filed: Dec. 18, 1995

[51] Int. Cl.⁶ .................. A61B 5/11; G01B 3/56
[52] U.S. Cl. .................. 33/512; 33/1 N; 128/778
[58] Field of Search .................. 33/1 N, 511, 512, 33/534; 128/774, 778

[56] References Cited

U.S. PATENT DOCUMENTS

| | | | |
|---|---|---|---|
| 3,038,258 | 6/1962 | Smialowski et al. | 33/512 |
| 3,815,247 | 6/1974 | Debrunner | 33/512 |
| 4,226,025 | 10/1980 | Wheeler | 33/512 |
| 5,038,489 | 8/1991 | Muehlenbein | 33/512 |
| 5,163,228 | 11/1992 | Edwards et al. | 33/1 N |
| 5,484,447 | 1/1996 | Waldock et al. | 33/511 |

FOREIGN PATENT DOCUMENTS

| | | | |
|---|---|---|---|
| 2622428 | 5/1989 | France | 128/778 |
| 1526647 | 12/1989 | U.S.S.R. | 128/778 |

*Primary Examiner*—G. Bradley Bennett
*Attorney, Agent, or Firm*—Donald D. Mon

[57] ABSTRACT

A goniometer responsive to the direction and angularity of movement of the protruding end of a rod that is partially inserted into the female urethra following a pelvic exertion. It includes a spirit level to establish a horizontal reference axis, and angle-measurement means to show the initial angle of the rod before exertion, and the new angle caused by the exertion.

5 Claims, 1 Drawing Sheet

GYNECOLOGICAL GONIOMETER

SPECIFICATION

1. Field of the Invention

A goniometer for use in the Q-Tip test used by gynecologists and urologists to learn the condition of the pelvic floor and whether prolapse exists of the urethrovesical junction.

2. Background of the Invention

Gynecologists and urologists routinely utilize a procedure familiarly called a Q-Tip test. This instrument utilizes a cotton-tipped rod of the type commonly known as a Q-Tip, although with a longer rod than that which is used in cosmetic work. Importantly, the cotton-bearing end is inserted into the urethra at its junction with the bladder while the patient is in a reclining position, with a substantial length of rod projecting from the urethral meatus. Then she is instructed to bear down or cough.

When she does, the rod will move either up or down, and through an angle whose direction and magnitude are of interest, because this provides important information about the woman's condition, specifically the degree of prolapse of the urethrovesical junction.

As it is presently conducted, the information provided is only whether the rod moves up or down, with some visual estimate of how far, especially if the procedure is repeated more than once. The problem is that there is no reliable reference from which measurement of the angle can be made, and that the motion is quite brief.

It is an object of this invention to provide a hand-held goniometer which includes a reference to the horizontal, and angle measurement means which can indicate the angle of the rod relative to that reference so the physician can measure the total angular movement and its direction from any arbitrary first location of the rod.

BRIEF DESCRIPTION OF THE INVENTION

A goniometer according to this invention includes a frame and a spirit level on the frame which when centered assures that an axis on the frame is horizontal. Angle measurement means such as a protractor is mounted to the frame with its central point on said axis and adjacent to an end of the frame. The angle indicia of the protractor radiate from the central point.

In use, with the Q-Tip inserted, the goniometer is placed with the central point alongside the rod and parallel to it, closely adjacent to the meatus, and the spirit level is brought to level. Now the angularity of the rod relative to the horizontal can be observed and recorded.

The woman then bears down, the pelvic floor moves, and the rod will move to a new position. The spirit level is kept centered, and the new angularity of the rod can be observed and recorded. From this data, the direction and change of angle can precisely be learned, to the advantage of both the physician and the patient, because a much more precise diagnosis can be made and more rational therapy can be planned.

According to a preferred but optional feature of the invention, two levers are pivotally mounted at the central point on opposite sides of the frame. One lever is set at the angle of the rod before the test. The other is responsive to the movement of the rod during the test. The difference in the angles will show both the direction and the angularity of movement.

The above and other features of this invention will be fully understood from the following detailed description and the accompanying drawings, in which:

DETAILED DESCRIPTION OF THE INVENTION

Figure 1:
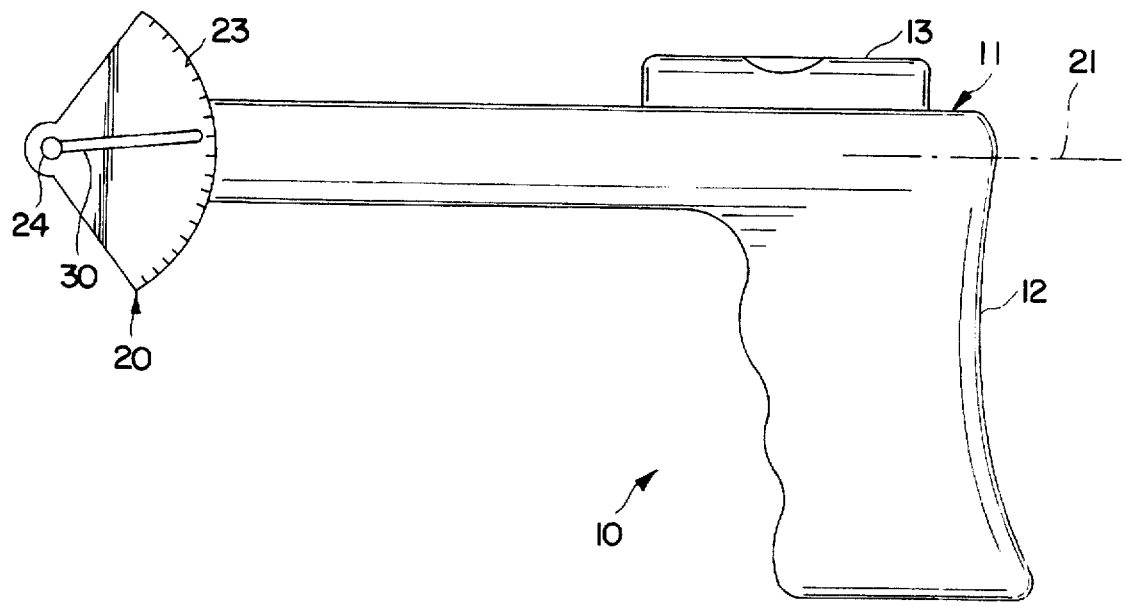
FIG. 1 is a side view of the goniometer in use in a test.
Figure 2:
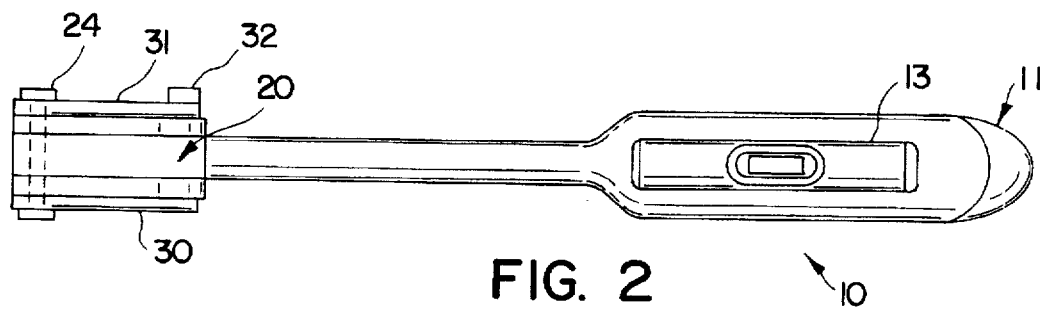
FIG. 2 is a top view of FIG. 1.

A goniometer 10 for use in the Q tip test is shown in FIG. 1. It has a frame 11 which conveniently is provided with a pistol-style type hand grip 12.

A conventional spirit level 13 is mounted to the top of the frame where it can conveniently be seen by the physician. It is fixed to the frame. When it is level, the centered position of the bubble in the tube assures that the axis of the frame is horizontal. When centered, all axes parallel to its indicated condition will also be horizontal, for example axis 21.

Angle measurement means 20 is mounted to the frame at an end thereof. Measurement means 20 may be a portion of a conventional protractor, with indicia 23 on its side surfaces to indicate angularity around a central point 24. Central point 24 will be located on axis 21, and the zero point of the protractor indicia will also be on axis 21, although this is not necessary. Also, it is not necessary to provide a full 180 degree protractor, because the range of movement of the rod is considerably less, and the female anatomy would interfere with certain segments beyond about 120 degrees. If desired the protractor can be made of transparent material, so that the indicia need be printed on only one side.

Levers 30, 31 are pivotally mounted to the goniometer at the central point. They are mounted with a light friction fit which will permit the levers to be rotated but hold their adjusted position. One of them (lever 31) will be movable by the rod without unduly restraining the rod, and will not over-travel. The other lever (lever 30) is never touched by the rod. The levers are preferably light-weight rigid wires.

Figure 3:
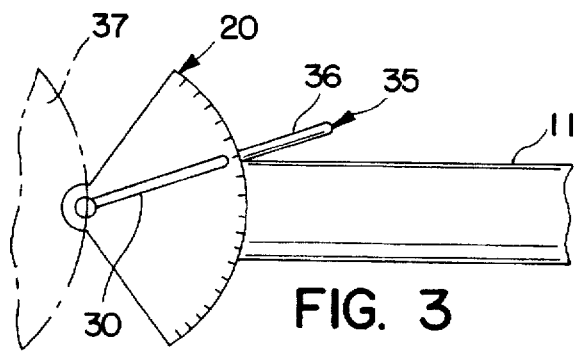
FIG. 3 is a schematic illustration of the use of the instrument with only the pertinent parts being shown.

In use as shown schematically in FIG. 3, a Q-tip 35 has been inserted into the urethra of a patient 37. Its rod 36 projects beyond the urethral meatus. The instrument is then placed with its central point closely adjacent to the meatus, and the frame is tilted until its bubble is centered. Then lever 30 is pivoted until it is parallel to the rod. This lever is preferably, but not necessarily, on the opposite side of the frame from the rod. It does not move once it is set.

Lever 31 has a flange 32 which projects laterally beyond it so it will be contacted by the rod. The physician will already have an idea which way the rod will move. With the spirit level still levelled, lever 31 is brought parallel to the rod with flange 32 in contact with the rod.

Figure 4:
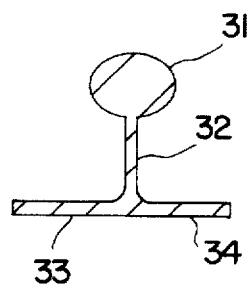
FIG. 4 is a fragmentary cross-section view showing a portion of one of the levers.

As shown in FIG. 4, flange 32 may be provided with a pair of oppositely directed fingers 33, 34 which can trap the rod so it does not slip off of the flange.

The woman is then told to bear down, or to cough, or to do whatever is needed to exercise (cause movement of) the pelvic floor. When she does so, in many cases the rod will move through an angle, moving lever 31 to a new position.

Then the angular readings of the two levers are read. Their deviations from the zero indicia are added, and this total angle is useful to the physician in making his diagnosis.

Should the physician have guessed wrong about the direction the rod would take, he simply repeats the procedure, this time placing flange 32 on the other side of the rod.

The levers are optional. The device is useful without them, but then it loses the advantage of retaining the readings. The motions are abrupt, and this feature is very useful, and does not require documenting or remembering the angles.

This elegantly simple device enables the physician for the first time to have a precise measurement of the patient's response to the Q-tip test. By making the reference axis part of the instrument, the instrument and its readings are independent of the fact that all women do not have "rest" angle readings that are horizontal or alike. Repeat tests on the same women are also independent of this fact, because the reference axis is independent of her position and orientation.

This invention is not to be limited by the embodiment shown in the drawings and described in the description, which is given by way of example and not of limitation, but only in accordance with the scope of the appended claims.

We claim:

1. A gynecological goniometer fop the Q-tip test comprising:

a frame;

a spirit level mounted to said frame which when leveled, establishes that a certain axis on the frame will be horizontal;

angle measurement means on said frame, said angle measurement means having a central point adjacent to an edge of the goniometer, said central point being disposed on said axis; and angle indicia on said angle measurement means radiating from said central point;

whereby with a Q-tip inserted in the urethra, its rod protruding, the frame may be brought adjacent to the urethral meatus and leveled, whereupon the physician may observe the initial angle of the rod, and upon pelvic exertion by the patient, observe its new angle, and thereby observe both the direction and angular extent of the deviation of the rod.

2. A goniometer according to claim 1 in which said measurement means is a portion of a protractor, said indicia being arranged on an arc centered on said central point.

3. A goniometer according to claim 1 in which a pair of levers are pivotally mounted to the frame at said central point, one of said levers including means to interfere with the rod when it moves so as to indicate the angular deviation of its movement, and the other lever being out of the path of the rod.

4. A goniometer according to claim 3 in which said measurement means is a portion of a protractor, said indicia being arranged in an arc centered on said central point.

5. A goniometer according to claim 3 in which said levers are on the opposite side of said frame from one another.

* * * * *